United States Patent [19]

Himmelsbach et al.

[11] Patent Number: 5,869,651
[45] Date of Patent: Feb. 9, 1999

[54] HYDRAZIDE DERIVATIVES OF POLYAMIDES AND THEIR MEDICAL USE AS CHELATING AGENTS

[75] Inventors: Richard J. Himmelsbach, Pleasanton, Calif.; Pål Rongved, Hellvik, Norway; Jo Klaveness, Oslo, Norway; Per Strande, Oslo, Norway; Harald Dugstad, Oslo, Norway

[73] Assignee: Nycomed Salutar, Sunnyvale, Calif.

[21] Appl. No.: 190,143

[22] PCT Filed: Jul. 16, 1992

[86] PCT No.: PCT/EP92/01598

§ 371 Date: Aug. 8, 1994

§ 102(e) Date: Aug. 8, 1994

[87] PCT Pub. No.: WO93/08045

PCT Pub. Date: Feb. 4, 1993

[30] Foreign Application Priority Data

Jul. 17, 1991 [GB] United Kingdom ............ 9115375

[51] Int. Cl.⁶ ............. C07D 498/08; C07F 15/02
[52] U.S. Cl. .......... 540/474; 540/465; 424/9.361; 534/15; 534/16
[58] Field of Search ............ 540/465, 474; 514/183

[56] References Cited

U.S. PATENT DOCUMENTS 5,322,681 6/1994 Klaveness .................. 424/9

FOREIGN PATENT DOCUMENTS

90/08134 7/1990 United Kingdom.

OTHER PUBLICATIONS

Gries et al, Chemical Abstract 109: 6552x for DE 3,625,417 (Feb. 11, 1988).

Gries et al., Chem. Abst 109: 6552x, 1988.

*Primary Examiner*—Mukund J. Shah
*Assistant Examiner*—Pavanaram K. Sripada
*Attorney, Agent, or Firm*—Fish & Richardson P.C.

[57] ABSTRACT

The invention relates to certain substituted derivatives of aminopolycarboxylic acids and metal chelates thereof. The compounds are particularly suitable for use as diagnostic agent. For example, the compounds can be used as radiodiagnostic agents, detoxification agents and contrast agents for diagnostic imaging processes. In particular, the high relaxivity paramagnetic metal chelates of substituted aminopolycarboxylic acids are especially suited for use as magnetic resonance imaging contrast agents.

16 Claims, No Drawings

HYDRAZIDE DERIVATIVES OF POLYAMIDES AND THEIR MEDICAL USE AS CHELATING AGENTS

This application is a 371 of PCT/EP 92/01598 F.D. Jul. 16, 1992.

The present invention relates to certain novel polyamine chelating agents, in particular to hydroxamate and hydrazide derivatives of polyamines, and to their uses, especially their medical uses.

The medical use of chelating agents is well established, for example as stabilizers for pharmaceutical preparations, as antidotes for poisonous heavy metal species and as diagnostic agents for the administration of metal species (e.g. ions or atoms) for diagnostic techniques such as X-ray, magnetic resonance imaging (MRI) or ultrasound imaging or scintigraphy.

Polyamine chelating agents, for example aminopoly (carboxylic acid or carboxylic acid derivative) (hereinafter APCA) chelating agents and their metal chelates, are well known and are described for example in U.S.A.-2407645 (Bersworth), U.S.A.-2387735 (Bersworth), EP-A-71564 (Schering), EP-A-130934 (Schering), EP-A-165728 (Nycomed AS), DE-A-2918842 (Rexolin Chemicals AB), DE-A-3401052 (Schering), EP-A-258616 (Salutar), DE-A-3633245 (Schering), EP-A-263059 (Schering), EP-A-277088 (Schering) and DE-A-3633243 (IDF).

Thus, for example, EP-A-71564 describes paramagnetic metal chelates, for which the chelating agents are nitrilotriacetic acid (NTA), N,N,N',N'-ethylenediaminetetraacetic acid (EDTA), N-hydroxyethyl-N,N',N'-ethylenediaminetriacetic acid (HEDTA), N,N,N',N'',N''-diethylenetriaminepentaacetic acid (DTPA) and N-hydroxyethylimino-diacetic acid, as being suitable as contrast agents for MRI, contrast being achieved by the effect of the magnetic field of the paramagnetic species (e.g. Gd(III)) with the chelating agents serving to reduce the toxicity and to assist administration of that paramagnetic species. Amongst the particular metal chelates disclosed by EP-A-71564 was GdDTPA, the use of which as an MRI contrast agent has recently received much attention. The Gd(III) chelate of 1,4,7,10-tetraazacyclododecanetetraacetic acid (DOTA), referred to in DE-A-3401052 (Schering) and in U.S.A.-4639365 (Sherry/University of Texas), has also recently received attention in this regard.

More recently, a number of modifications to the basic APCA structures have been proposed to provide chelating agents with improved stability, water solubility, selectivity or toxicity. This includes for example providing hydrophilic substituents as described by Nycomed in EP-A-299795 or altering the structure of bridging chains between the amine nitrogens as described by Schering in EP-A-250358.

In the field of hepatobiliary MRI contrast agents, where lipophilicity is desired, Nycomed (in EP-A-165728) have proposed the use of paramagnetic chelates of certain anilide group-containing iminodiacetic acids and Lauffer in WO-A-86/06605 has suggested the use of paramagnetic chelates of triaza and tetraaza macrocycles which carry a fused aromatic ring but are otherwise unsubstituted.

However, all hitherto known APCA chelating agents and their metal chelates encounter problems of toxicity, stability, selectivity or suppressed relaxivity and there is thus a general and continuing need for such polyamine chelating agents which form metal chelates of reduced toxicity or improved stability, water solubility, selectivity or relaxivity.

We have now found that certain substituted derivatives of aminopolycarboxylic acids and metal chelates thereof are particularly suitable for use as diagnostic and therapeutic agents, for example as radiotherapeutic agents, as detoxification agents and as contrast agents for diagnostic imaging processes. In particular we have found that high relaxivity paramagnetic metal chelates of such substituted APCA derivatives are especially suited for use as MRI contrast agents.

In one aspect the present invention therefore provides a compound of formula I $$A[X(CR^1R^2)_n]_mXA \qquad (I)$$

or a chelate complex or salt thereof, for use as therapeutic or diagnostic agent wherein in formula I, each of the groups $R^1$ and $R^2$ may independently represent a hydrogen atom or an alkyl or alkoxy group, optionally carrying one or more substituents selected from hydroxy, alkoxy and aryl groups;

each X independently represents an oxygen or sulphur atom or, preferably, a group NA;

each A independently represents a hydrogen atom or an alkyl group optionally substituted by a group Y;

each Y represents a hydrogen atom, or a group Z, COZ, $SO_3R^6$, CSZ, $PO_2Z$ or B;

or one or more pairs of A groups on different X moieties may together form a group $[(CR^1R^2)_nX^1]_p(CR^1R^2)_n$ or a group A on a mid-chain nitrogen may represent a group $[(CR^1R^2)_nX^1]_p(CR^1R^2)_nX^1A$ where p represents an integer of 0 to 6, preferably 0, and each $X^1$ independently represents an oxygen or sulphur atom or a group $NA^1$ where $A^1$ is as defined for A but may not form part of a group attached to more than one nitrogen atom;

or two adjacent groups $R^1$ and/or A may together form a homo- or heterocyclic saturated or unsaturated 5–7 membered ring containing 0, 1 or 2 ring heteroatoms selected from oxygen, nitrogen and sulphur;

each group B represents a group $CONR^7(OR^8)$, $CONR^7(NR^8_2)$, $PO(NR^7R^8)_2$, $SO_2R^7$, $SO_2NR^7R^8$ or $NO_2$;

each group Z independently represents a group $OR^6$, $SR^6$ or $NR^6_2$;

each of the groups $R^6$ independently represents a hydrogen atom, or an alkyl group optionally substituted by one or more hydroxy, alkoxy or aryl groups;

each of the groups $R^7$ and $R^8$ independently represents a group $R^6$, an aryl group optionally substituted by one or more hydroxy or alkoxy groups or a lipophilic group M, preferably incorporating or linked via a hydrolysable (e.g. ester) linkage;

m is an integer of 2 to 8, preferably 2, 3 or 4;

n is an integer of 2 to 4, preferably 2 or 3, especially 2;

with the provisos that where the compound of formula I is linear and each X is NA and two terminal A groups carry Y groups of formula $CON(OR^8)R^7$, then in said terminal A groups (i) if $R^8$ is hydrogen $R^7$ is other than hydrogen or $C_{1-3}$ alkyl (preferably other than unsubstituted alkyl) and (ii) if $R^7$ is alkoxylated alkyl $R^8$ is other than methyl (preferably other than unsubstituted alkyl), that at least two, preferably at least three non-B ionisable Y groups are present, that at least one Y group represents a non-ionisable group B, and preferably that if each X is a group NA and each group A is Y-containing (especially where m is 2 and each A is a group —$CH_2Y$) and two groups A contain B groups then if these B groups are $CONHNR_2^8$ one or more $R^8$ group is other than methyl (preferably other than unsubstituted $C_{1-3}$ alkyl).

In a further aspect the present invention also provides a compound of formula Ic

   (Ic)

or a chelate complex or salt thereof
(wherein in formula Ic,
each X represents a group NA;
each A independently represents a hydrogen atom or an alkyl group optionally substituted by a group Y,
or the two terminal A groups together form a group $[(CH_2)_2X^1](CH_2)_2$ where $X^1$ represents a group $NA^1$ where $A^1$ is as defined for A but may not form part of a group attached to more than one nitrogen atom;
each Y represents a hydrogen atom, or a group Z, COZ, $SO_3R^6$, CSZ, $PO_2Z$ or B;
each group B represents a group $CONR^7(OR^8)$, $CONR^7(NR^8{}_2)$, $PO(NR^7R^8)_2$, $SO_2R^7$, $SO_2NR^7R^8$ or $NO_2$;
each group Z independently represents a group $OR^6$, $SR^6$ or $NR^6{}_2$;
each of the groups $R^6$ independently represents a hydrogen atom, or an alkyl group optionally substituted by one or more hydroxy, alkoxy or aryl groups;
each of the groups $R^7$ and $R^8$ independently represents a group $R^6$, an aryl group optionally substituted by one or more hydroxy or alkoxy groups or a lipophilic group M, preferably incorporating or linked via a hydrolysable (e.g. ester) linkage;
with the provisos that where the compound of formula I is linear and two terminal A groups carry Y groups of formula $CON(OR^8)R^7$, then in said terminal A groups (i) if $R^8$ is hydrogen $R^7$ is other than hydrogen or $C_{1-3}$ alkyl (preferably other than unsubstituted alkyl) and (ii) if $R^7$ is alkoxylated alkyl $R^8$ is other than methyl (preferably other than unsubstituted alkyl), that at least two, preferably at least three non-B ionisable Y groups are present, that at least one Y group represents a non-ionisable group B, and preferably that if each X is a group NA and each group A is Y-containing (especially where each A is a group $—CH_2Y$) and two groups A contain B groups then if these B groups are $CONHNR_2^8$ one or more $R^8$ group is other than methyl (preferably other than unsubstituted $C_{1-3}$ alkyl).

In formulae I and Ic, ionisable groups Y are preferably carboxyl or carboxylate groups and alkyl and alkylene moieties in groups A, $A^1$, $R^1$, $R^2$, $R^6$, $R^7$ and $R^8$ may be saturated or unsaturated (but preferably saturated) straight-chained or branched and preferably contain from 1 to 8, especially preferably 1 to 6, and most preferably 1 to 3, carbon atoms. Alkyl moieties in Y-substituted A and $A^1$ groups are preferably ethyl or more especially methyl groups.

Groups $R^7$ and $R^8$ in the B groups $—SO_2NR^7R^8$, $—PO(NR^7R^8)_2$ and $—SO_2R^7$ are preferably non-labile hydrogen or branched or linear $C_{1-6}$ alkyl (especially $C_{1-3}$ alkyl) optionally mono or polyhydroxylated and/or mono or poly $C_{1-3}$-alkoxylated or substituted by aryl, e.g. phenyl, groups.

Aryl and arylene groups present in the compounds of the invention are preferably mono or bicyclic containing. 5 to 7 ring atoms in the or each ring, and where the groups are heterocyclic each ring preferably contains 1 or 2 ring heteroatoms selected from O, N and S.

The lipophilic groups M mentioned above may be any of the groups conventionally used to increase the lipophilicity of a molecule and preferably include aryl groups such as benzyl or phenyl groups, alkaryl groups and saturated branched or unbranched acyclic hydrocarbon groups (e.g. alkyl groups), especially such groups containing from 6 to 22, particularly 8 to 20 and more particularly 12 to 18 carbon atoms. As previously mentioned, it is especially preferred that any lipophilic group be linked by a readily hydrolysable linkage. Ester linkages are particularly preferred in this regard and thus preferred lipophilic groups M include the following:

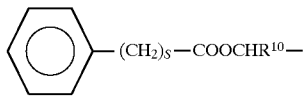

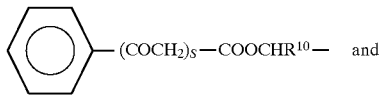 and (where s represents an integer of 1 to 3 and $R^{10}$ represents hydrogen or an optionally hydroxyl or alkoxy substituted alkyl group).

Where the compounds of formulae I or Ic are linear, or branched (ie. where they contain no linking group $[(CR^1R^2)_nX^1]_p (CR^1R^2)_n)$ it is preferred that the B groups occur at terminal A groups.

Linear compounds of Formulae I or Ic carrying two B groups, one at each terminus, are especially preferred. Moreover, in such linear compounds, it is particularly preferred that the two B groups be the same.

In macrocyclic compounds of formulae I or Ic it is preferred that one, two or three of the macrocyclic X groups include B groups. Such macrocyclic compounds moreover preferably contain 3, 4 or 5, especially 4, heteroatoms in the macrocyclic ring skeleton. DO3A derivatives are especially preferred.

The compounds of formulae I or Ic where Y is a carboxyl group can conveniently form salts or chelates in which Y represents —COOMt (wherein $Mt^+$ is a monovalent cation or a fraction of a polyvalent cation, for example an ammonium or substituted ammonium ion or a metal ion, for example an alkali metal or alkaline earth metal ion). Particularly preferably, Mt+ is a cation deriving from an organic base, for example meglumine or lysine. In such salts or chelates one or more (but not necessarily all) of the carboxyl groups are transformed into COOMt groups.

It is particularly preferred that the number of the ion-forming groups Y in the compounds of formulae I or Ic be chosen to equal the valency of the metal species to be chelated by the compound of formula I or Ic. Thus, for example, where Gd(III) is to be chelated, the compound of formulae I or Ic (or salt thereof) preferably contains three ion-forming Y groups, for example —COOH (or —COOMt). In this way, the metal chelate will be formed as a neutral species, a form preferred since the osmolalities in concentrated solutions of such compounds are low and since their toxicities relative to their ionic analogues are significantly reduced.

Particularly preferred compounds according to the invention include non-ionic metal chelates, especially paramagnetic metal chelates, of compounds of formulae I or Ic in which the donor (coordinating) atoms are APCA skeleton nitrogens and Y group oxyacid (e.g. carboxylate) oxygens and especially those in which the B groups do not function as charged, metal coordinating moieties. More especially, the compounds of formulae I or Ic preferably contain at least two non-ionizable B groups. By non-ionizable it is meant that in aqueous solution at physiological pH the group is substantially uncharged. Accordingly it is particularly preferred that the compounds of formulae I or Ic and their metal chelates should contain at least one, preferably at least two, B groups which contain no protons having a pKa of less than 8, particularly preferably none having pKa's of less than 8.5 or more especially 9 or 9.5. Thus such B groups preferably do not contain labile hydrogens. In chelate complexes of the compounds of formulae I or Ic these B groups, which preferably are the only B groups present, will not function as charged donor groups for the chelated metal ions but may participate in metal coordination and in the bonding of solvent water molecules in the first co-ordination sphere and thereby in the transfer of magnetic information and consequently they are important in the realisation of enhanced relaxivity.

Enhanced relaxivity for MRI contrast agents enables lower dosages to be used in order to achieve a particular contrast effect thus increasing the safety margin for the MRI investigation. The hydroxamate chelates according to the present invention are especially attractive in this regard and appear to represent a particularly improved class of third generation CNS agents.

Especially preferred compounds according to the invention include those of formulae Ia and Ib

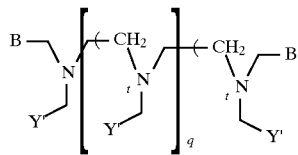

(Ic)

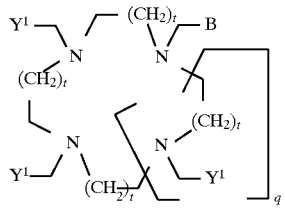

(Ib)

where q is 0, 1 or 2, preferably 1, t is 1 or 2, preferably 1, and $Y^1$ is an ion forming Y group, preferably a carboxyl or carboxylate group.

In the compounds of formulae Ia and Ib, the following are preferred as identities for B
    —CO—NH—$NH_2$
    —CO—NH—$N(CH_3)_2$
    —CO—$NCH_3$—$NH_2$
    —CO—$NCH_3$—$N(CH_3)_2$
    —CO—$NR^{7'}$—$OR^{8'}$
    —CO—$NCH_3$—$OR^{8'}$
    —$SO_2N(CH_3)_2$
    —$PO(N(CH_3)_2)_2$
    —$SO_2CH_3$
    —$NO_2$
where $R^{7'}$ is an optionally substituted alkyl or aryl group or a lipophilic group M and $R^{8'}$ is hydrogen, methyl, benzyl, or

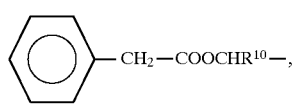

or $(CH_3)_3CCOOCHR^{10}$—(where $R^{10}$ is as defined above) the phenyl moieties of which are optionally substituted by hydroxy, alkoxy, alkoxyalkyl, hydroxyalkyl, hydroxyalkoxy or alkoxyalkoxy groups.

Particularly preferred compounds according to the invention include derivatives of DTPA and DO3A of formulae Ia' and Ib'

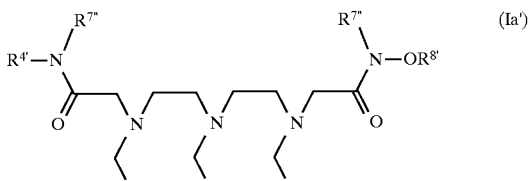

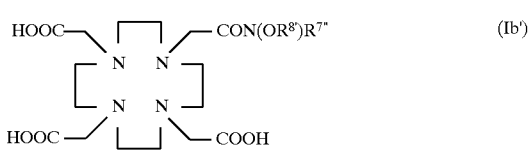

where $R^{7''}$ is a lipophilic group, eg. an alkyl, aryl, aralkyl or alkaryl group, and $R^{8'}$ is as defined above, and preferably $R^{8'}$ is hydrogen.

The compounds of the invention may be prepared by reacting a reactive derivative of the corresponding aminopolycarboxylic acid with an appropriately substituted hydroxylamine or hydrazide, or by reacting a corresponding amine with an appropriately substituted alkylating agent.

Suitable reactive derivatives include anhydrides and esters.

Thus viewed from a further aspect the present invention provides a process for the preparation of compounds according to the invention, said process comprising one or more of the following steps (i) reacting a compound of formula II

(where X" is a group X, a protected group X or a group NA''';

A" is a group A, a protected group A or a group A''';

A''' is an alkyl group attached to an activated carboxyl or phosphono group;

$R^{1''}$ and $R^{2''}$ are each groups $R^1$ or $R^2$ or protected groups $R^1$ and $R^2$ respectively;

with the proviso that at least one group A''', and preferably at least two such groups, is/are present)

with an amine derivative of formula III

(where B" is a group $NR^7(OR^8)$, $NR^7NR^8_2$ or $NR^7R^8$ or a protected such group), followed if required by the removal of any protecting groups;

(ii) reacting a compound of formula IV

(where A* is a group A, a protected group A or a hydrogen atom;

X* is a group X, a protected group X or a group NA*, and $R^{1''}$, $R^{2''}$, n and m are as hereinbefore defined, with the proviso that at least one A*, preferably two, is hydrogen) with a compound of formula V $$Lv-A^{**} \quad (V)$$

(where Lv is a leaving group, e.g. a halogen atom, and A** is a Y-containing A or protected A group) followed if required by removal of any protecting groups;

(iii) converting a compound of formula I into a salt thereof or a salt of a compound of formula I into the free acid or base; and (iv) converting a compound of formula I or salt thereof into a chelate complex thereof.

The starting compounds of formulae II and III mentioned above are either known from the literature, for example the patent publications from 1983 of Salutar Inc, Nycomed AS, Bracco, Guerbet, Schering, Squibb and Mallinckrodt such as those mentioned above and the documents mentioned therein, or may be prepared from known compounds by standard procedures.

The activated carboxyl and phosphono groups in the compounds of formula II may be any derivatives capable of reacting with an amine to produce a peptide or phosphonamide linkage, e.g. an acid anhydride or acid halide group. These may be generated by conventional techniques.

Thus for example cyclic acid anhydrides and their cyclic amide derivatives and APCA esters may be used as the starting materials of formulae II and III as exemplified by the following reaction schemes:

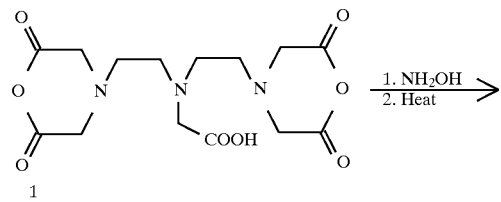

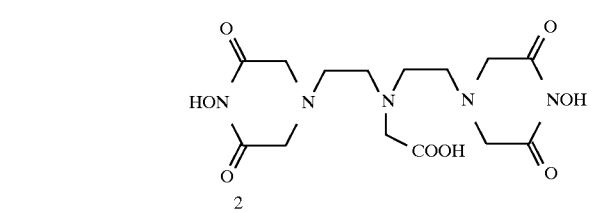

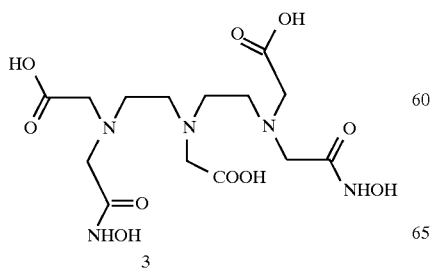

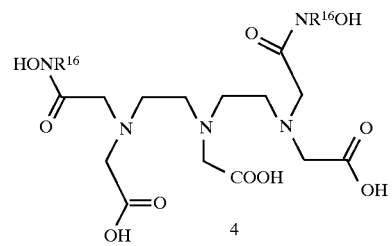

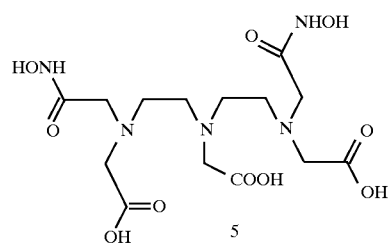

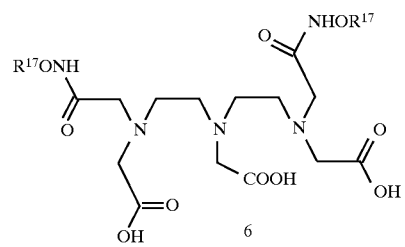

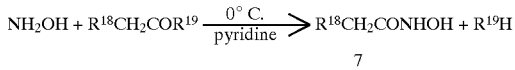

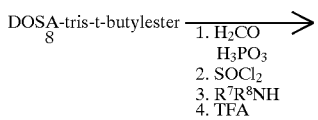
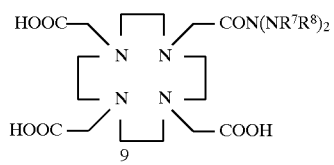

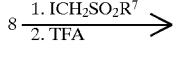
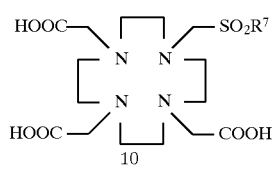

-continued

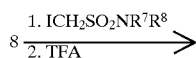

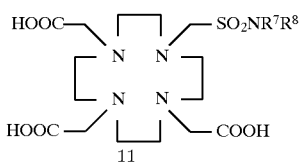

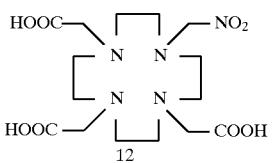

where $R^{16}$ and $R^{17}$ are substituent groups desired to be introduced, $R^{18}$ is a halogen atom and $R^{19}$ is a halogen atom or an alkoxy or acyl group.

The substituents not taking part in amide linkage formation may of course require protection, eg. hydroxyl groups may need to be converted to ester groups, during the initial reaction in step (i). Conventional protection and deprotection techniques may be used, see for example "Protective Groups in Organic Synthesis" by T. W. Greene, Wiley-Interscience, NY, 1981 and "Protective Groups in Organic Chemistry" by J. F. W. McOmie, Plenum, London, 1973.

Salt and chelate formation may be effected by conventional techniques, e.g. as described in the above mentioned patent publications.

The chelants of formula I may be used as the basis for bifunctional chelants or for polychelant compounds, that is compounds containing several independent chelant groups, by substituting for one A, $A^1$, $R^1$, $R^2$, $R^7$ or $R^8$ group a bond or linkage to a macromolecule or polymer, e.g. a tissue specific biomolecule or a backbone polymer such as polylysine or polyethyleneimine which may carry several chelant groups and may itself be attached to a macromolecule to produce a bifunctional-polychelant. Such macromolecular derivatives of the compounds of formula I and the metal chelates and salts thereof form a further aspect of the present invention.

The linkage of a compound of formula I to a macromolecule or backbone polymer may be effected by the methods of Salutar (WO-A-90/12050) or by any of the conventional methods such as the carbodiimide method, the mixed anhydride procedure of Krejcarek et al. (see Biochemical and Biophysical Research Communications 77: 581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 for example) and by the use of linker molecules as described for example by Nycomed in WO-A-89/06979.

Salt and chelate formation may be performed in a conventional manner. The chelating agents of formula I are particularly suitable for use in detoxification or in the formation of metal chelates, chelates which may be used for example in or as contrast agents for in vivo or in vitro magnetic resonance (MR), X-ray or ultrasound diagnostics (e.g. MR imaging and MR spectroscopy), or scintigraphy or in or as therapeutic agents for radiotherapy, and such uses of these metal chelates form a further aspect of the present invention.

Salts or chelate complexes of the compounds of the invention containing a heavy metal atom or ion are particularly useful in diagnostic imaging or therapy. Especially preferred are salts or complexes with metals of atomic numbers 20–32, 42–44, 49 and 57 to 83, especially Gd, Dy and Yb. For use as an MR-diagnostics contrast agent, the chelated metal species is particularly suitably a paramagnetic species, the metal conveniently being a transition metal or a lanthanide, preferably having an atomic number of 21–29, 42, 44 or 57–71. Metal chelates in which the metal species is Eu, Gd, Dy, Ho, Cr, Mn or Fe are especially preferred and $Gd^{3+}$, $Mn^{2+}$ and $Dy^{3+}$ are particularly preferred. Chelates of ions of these metals specifically listed above with chelants of formula I or their salts with physiologically tolerable counterions are particularly useful for the diagnostic imaging procedures mentioned herein and they and their use are deemed to fall within the scope of the invention and references to chelates of compounds of formula I herein are consequently to be taken to include such chelates.

For diagnostic imaging purposes it is particularly important that the metal chelate complex be as stable as possible to prevent dissociation of the complex in the body. It is noted in this regard that the hydroxamate and hydrazide derivatives of the invention form particularly stable complexes with the metal ions of greatest interest in MRI and thus such chelates are particularly suitable for use as diagnostic imaging contrast agents.

In magnetic resonance imaging (MRI) it is frequently desirable to be able to target certain organs or tissues. In particular there is a need for improved hepatobiliary imaging MR contrast agents. Chelates of paramagnetic metals with compounds of formula I where one or more of the $R^7$ or $R^8$ groups in the groups COB are lipophilic groups M are particularly suited for use as hepatobiliary MR contrast agents, since the presence of the lipophilic group will promote uptake by hepatocytes. By linking the lipophilic group to the molecule via a readily hydrolysable linking group such as an ester, the reabsorption after excretion to the intestine can be prevented.

For certain hepatobiliary imaging purposes it is desirable that the lipophilic contrast agent be precipitated as particles which can be taken up by Kupffer cells in the liver. In such cases it is preferred to use chelates of $Dy^{3+}$ with lipophilic compounds of formula I in conjunction with an imaging system utilising the magnetic susceptibility properties of the contrast agent; Kupffer cells in the liver are scarce and the contrast achievable using chelates with the gadolinium normally used in conventional MR imaging (i.e. as a $T_1$ relaxation agent) is generally insufficient. Such magnetic susceptibility agents form an important embodiment of the invention.

For use as contrast agents in MRI, the paramagnetic metal species is conveniently non-radioactive as radioactivity is a characteristic which is neither required nor desirable for MR-diagnostic contrast agents. For use as X-ray or ultrasound contrast agents, the chelated metal species is preferably a heavy metal species, for example a non-radioactive metal with an atomic number greater than 37, preferably greater than 50, e.g. $Dy^{3+}$.

For use in scintigraphy and radiotherapy, the chelated metal species must of course be radioactive and any conventional complexable radioactive metal isotope, such as $^{99m}Tc$, $^{67}Ga$ or $^{111}In$ for example, may be used. For radiotherapy, the chelating agent may be in the form of a metal chelate with for example $^{153}Sm$, $^{67}Cu$ or $^{90}Y$.

For use in detoxification of heavy metals, the chelating agent should be in salt form with a physiologically acceptable counterion, e.g. sodium, calcium, ammonium, zinc or meglumine, e.g. as the sodium salt of the chelate of the compound of formula I with zinc or calcium.

Where the metal chelate carries an overall charge, such as is the case with the prior art Gd DTPA, it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

Viewed from a further aspect, the present invention provides a diagnostic or therapeutic agent comprising a metal chelate, whereof the chelating entity is the residue of a compound according to the present invention, together with at least one pharmaceutical or veterinary carrier or excipient, or adapted for formulation therewith or for inclusion in a pharmaceutical formulation for human or veterinary use.

Viewed from another aspect, the present invention provides a detoxification agent comprising a chelating agent according to the invention in the form of a weak complex or salt with a physiologically acceptable counterion, together with at least one pharmaceutical or veterinary carrier or excipient, or adapted for formulation therewith or for inclusion in a pharmaceutical formulation for human or veterinary use.

The diagnostic and therapeutic agents of the present invention may be formulated with conventional pharmaceutical or veterinary formulation aids, for example stabilizers, antioxidants, osmolality adjusting agents, buffers, pH adjusting agents, etc. and may be in a form suitable for parenteral or enteral administration, for example injection or infusion or administration directly into a body cavity having an external escape duct, for example the Gastrointestinal tract, the bladder or the uterus. Thus the agent of the present invention may be in a conventional pharmaceutical administration form such as a tablet, capsule, powder, solution, suspension, dispersion, syrup, suppository, etc; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g. 0.01 to 10 mole percent) of chelants (such as, for example, DTPA, DTPA-bisamide or non-complexed chelants of formula I) or calcium chelate complexes (as for example calcium DTPA, CaNaDTPA-bisamide, calcium salts or chelates of chelants of formula I), or, optionally, additions (e.g. 1 to 50 mole percent) of calcium or sodium salts (for example, calcium chloride, calcium ascorbate, calcium gluconate or calcium lactate combined with metal chelate complexes of chelants of formula I and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

For MRI and for X-ray imaging of some portions of the body the most preferred mode for administering metal chelates as contrast agents is parenteral, e.g. intravenous administration. Parenterally administrable forms, e.g. intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Where the diagnostic or therapeutic agent comprises a chelate or salt of a toxic metal species, e.g. a heavy metal ion, it may be desirable to include within the formulation a slight excess of the chelating agent, e.g. as discussed by Schering in DE-A-3640708, or more preferably a slight excess of the calcium salt of such a chelating agent.

For MR-diagnostic examination, the diagnostic agent of the present invention, if in solution, suspension or dispersion form, will generally contain the metal chelate at concentration in the range 1 micromole to 1.5 mole per liter, preferably 0.1 to 700 mM. The diagnostic agent may however be supplied in a more concentrated form for dilution prior to administration. The diagnostic agent of the invention may conveniently be administered in amounts of from $10^{-3}$ to 3 mmol of the metal species per kilogram of body weight, e.g. about 1 mmol Dy/kg bodyweight.

For X-ray examination, the dose of the contrast agent should generally be higher and for scintigraphic examination the dose should generally be lower than for MR examination. For radiotherapy and detoxification, conventional dosages may be used.

Viewed from a further aspect, the present invention provides a method of generating enhanced images of the human or non-human animal body, which method comprises administering to said body a diagnostic agent comprising a metal chelate of compound of formula I $$A\ [X(CR^1R^2)_n]_m XA \qquad (I)$$

(wherein in formula I, each of the groups $R^1$ and $R^2$ may independently represent a hydrogen atom or an alkyl or alkoxy group, optionally carrying one or more substituents selected from hydroxy, alkoxy and aryl groups;

each X independently represents an oxygen or sulphur atom or, preferably, a group NA;

each A independently represents a hydrogen atom or an alkyl group optionally substituted by a group Y;

or one or more pairs of A groups on different X moieties may together form a group $[(CR^1R^2)_n X^1]_p (CR^1R^2)_n$ or a group A on a mid-chain nitrogen may represent a group $[(CR^1R^2)_n X^1]_p (CR^1R^2)_n X^1 A$ where p represents an integer of 0 to 6, preferably 0, and each $X^1$ independently represents an oxygen or sulphur atom or a group $NA^1$ where $A^1$ is as defined for A but may not form part of a group attached to more than one nitrogen atom;

or two adjacent groups $R^1$ and/or A may together form a homo- or heterocyclic saturated or unsaturated 5-7 membered ring containing 0, 1 or 2 ring heteroatoms selected from oxygen, nitrogen and sulphur;

each Y represents a hydrogen atom, or a group Z, COZ, $SO_3R^6$, CSZ, $PO_2Z$ or B;

each group B represents a group $CONR^7(OR^8)$, $CONR^7(NR^8{}_2)$, $PO(NR^7R^8)_2$, $SO_2NR^7R^8$, $SO_2R^7$ or $NO_2$;

each group Z independently represents a group $OR^6$, $SR^6$ or $NR^6{}_2$;

each of the groups $R^6$ independently represents a hydrogen atom, or an alkyl group optionally substituted by one or more hydroxy or alkoxy groups;

each of the groups $R^7$ and $R^8$ independently represents a group $R^6$, an aryl group optionally substituted by one or more hydroxy or alkoxy groups or a lipophilic group M, preferably incorporating or linked via a hydrolysable (e.g. ester) linkage;

m is an integer of 2 to 8, preferably 2, 3 or 4;

n is an integer of 2 to 4, preferably 2 or 3, especially 2;

with the provisos that where the compound of formula I is linear and each X is NA and two terminal A groups carry Y groups of formula $CON(OR^8)R^7$, then in said terminal A groups (i) if $R^8$ is hydrogen $R^7$ is other than methyl (preferably other than hydrogen or unsubstituted alkyl, especially $C_{1-3}$ alkyl) and (ii) if $R^7$ is alkoxylated alkyl $R^8$ is other than methyl (preferably other than unsubstituted alkyl), and that at least two, preferably at least three, ionisable non-B Y groups are present and that at least one Y group represents a non-ionizable group B).

Viewed from a further aspect, the present invention provides a method of radiotherapy practised on the human or non-human animal body, which method comprises administering to said body a chelate of a radioactive metal species with a chelating agent of formula I

(wherein in formula I, each of the groups $R^1$ and $R^2$ may independently represent a hydrogen atom or an alkyl or alkoxy group, optionally carrying one or more substituents selected from hydroxy, alkoxy and aryl groups;

each X independently represents an oxygen or sulphur atom or, preferably, a group NA;

each A independently represents a hydrogen atom or an alkyl group optionally substituted by a group Y;

or one or more pairs of A groups on different X moieties may together form a group $[(CR^1R^2)_nX^1]_p(CR^1R^2)_n$ or a group A on a mid-chain nitrogen may represent a group $[(CR^1R^2)_nX^1]_p(CR^1R^2)_nX^1A$ where p represents an integer of 0 to 6, preferably 0, and each $X^1$ independently represents an oxygen or sulphur atom or a group $NA^1$ where $A^1$ is as defined for A but may not form part of a group attached to more than one nitrogen atom;

or two adjacent groups $R^1$ and/or A may together form a homo- or heterocyclic saturated or unsaturated 5-7 membered ring containing 0, 1 or 2 ring heteroatoms selected from oxygen, nitrogen and sulphur;

each Y represents a hydrogen atom, or a group Z, COZ, $SO_3R^6$, CSZ, $PO_2Z$ or B;

each group B represents a group $CONR^7(OR^8)$, $CONR^7(NR^8{}_2)$, $PO(NR^7R^8)_2$, $SO_2NR^7R^8$, $SO_2R^7$ or $NO_2$;

each group Z independently represents a group $OR^6$, $SR^6$ or $NR^6{}_2$;

each of the groups $R^6$ independently represents a hydrogen atom, or an alkyl group optionally substituted by one or more hydroxy or alkoxy groups;

each of the groups $R^7$ and $R^8$ independently represents a group $R^6$, an aryl group optionally substituted by one or more hydroxy or alkoxy groups or a lipophilic group M, preferably incorporating or linked via a hydrolysable (e.g. ester) linkage;

m is an integer of 2 to 8, preferably 2, 3 or 4;

n is an integer of 2 to 4, preferably 2 or 3, especially 2;

with the provisos that where the compound of formula I is linear and each X is NA and two terminal A groups carry Y groups of formula $CON(OR^8)R^7$, then in said terminal A groups (i) if $R^8$ is hydrogen $R^7$ is other than methyl (preferably other than hydrogen or unsubstituted alkyl, especially $C_{1-3}$ alkyl) and (ii) if $R^7$ is alkoxylated alkyl $R^8$ is other than methyl (preferably other than unsubstituted alkyl), and that at least two, preferably at least three, ionisable non-B Y groups are present and that at least one Y group represents a non-ionizable group B).

Viewed from a further aspect, the present invention provides a method of heavy metal detoxification practised on the human or non-human animal body, which method comprises administering to said body a chelating agent of formula I

(wherein in formula I, each of the groups $R^1$ and $R^2$ may independently represent a hydrogen atom or an alkyl or alkoxy group, optionally carrying one or more substituents selected from hydroxy, alkoxy and aryl groups;

each X independently represents an oxygen or sulphur atom or, preferably, a group NA;

each A independently represents a hydrogen atom or an alkyl group optionally substituted by a group Y;

or one or more pairs of A groups on different X moieties may together form a group $[(CR^1R^2)_nX^1]_p(CR^1R^2)_n$ or a group A on a mid-chain nitrogen may represent a group $[(CR^1R^2)_nX^1]_p(CR^1R^2)_nX^1A$ where p represents an integer of 0 to 6, preferably 0, and each $X^1$ independently represents an oxygen or sulphur atom or a group $NA^1$ where $A^1$ is as defined for A but may not form part of a group attached to more than one nitrogen atom;

or two adjacent groups $R^1$ and/or A may together form a homo- or heterocyclic saturated or unsaturated 5-7 membered ring containing 0, 1 or 2 ring heteroatoms selected from oxygen, nitrogen and sulphur;

each Y represents a hydrogen atom, or a group Z, COZ, $SO_3R^6$, CSZ, $PO_2Z$ or B;

each group B represents a group $CONR^7(OR^8)$, $CONR^7(NR^8{}_2)$, $PO(NR^7R^8)_2$, $SO_2NR^7R^8$, $SO_2R^7$ or $NO_2$;

each group Z independently represents a group $OR^6$, $SR^6$ or $NR^6{}_2$;

each of the groups $R^6$ independently represents a hydrogen atom, or an alkyl group optionally substituted by one or more hydroxy or alkoxy groups;

each of the groups $R^7$ and $R^8$ independently represents a group $R^6$, an aryl group optionally substituted by one or more hydroxy or alkoxy groups or a lipophilic group M, preferably incorporating or linked via a hydrolysable (e.g. ester) linkage;

m is an integer of 2 to 8, preferably 2, 3 or 4;

n is an integer of 2 to 4, preferably 2 or 3, especially 2;

with the provisos that where the compound of formula I is linear and each X is NA and two terminal A groups carry Y groups of formula $CON(OR^8)R^7$, then in said terminal A groups (i) if $R^8$ is hydrogen $R^7$ is other than methyl (preferably other than hydrogen or unsubstituted alkyl, especially $C_{1-3}$ alkyl) and (ii) if $R^7$ is alkoxylated alkyl $R^8$ is other than methyl (preferably other than unsubstituted alkyl), and that at least two, preferably at least three, ionisable non-B Y groups are present and that at least one Y group represents a non-ionizable group B), or a physiologically tolerable salt or weak complex thereof.

Preferred for use in such methods are compounds of Formula I, Ia, Ib, Ia', Ib' and Ic, as defined above with the provisos that where the compound of formula I is linear and each X is NA and two terminal A groups carry Y groups of formula $CON(OR^8)R^7$, then in said terminal A groups (i) if $R^8$ is hydrogen R7 is other than methyl (preferably other than hydrogen or unsubstituted alkyl, especially $C_{1-3}$ alkyl) and (ii) if $R^7$ is alkoxylated alkyl $R^8$ is other than methyl (preferably other than unsubstituted alkyl), and that at least two, preferably at least three, ionisable non-B Y groups are present and that at least one Y group represents a non-ionizable group B).

Viewed from a yet further aspect, the present invention also provides the use of the compounds, especially the metal chelates, according to the invention for the manufacture of diagnostic or therapeutic agents for use in methods of image generation, detoxification or radiotherapy practised on the human or non-human animal body.

Viewed from a still further aspect, the present invention provides a process for the preparation of the metal chelates of the invention which process comprises admixing in a solvent a compound of formula I or a salt (e.g. the sodium salt) or chelate thereof together with an at least sparingly soluble compound of said metal, for example a chloride, oxide, acetate or carbonate.

Viewed from a yet still further aspect, the present invention provides a process for the preparation of the diagnostic or therapeutic agent of the present invention, which comprises admixing a metal chelate according to the invention, or a physiologically acceptable salt thereof, together with at least one pharmaceutical or veterinary carrier or excipient.

Viewed from a yet still further aspect, the present invention provides a process for the preparation of the detoxification agent of the invention, which comprises admixing a chelating agent according to the invention, preferably in the form of a salt with a physiologically acceptable counterion, together with at least one pharmaceutical or veterinary carrier or excipient.

The disclosures of all of the documents mentioned herein are incorporated by reference.

The present invention will now be illustrated further by the following non-limiting Examples. All ratios and percentages given herein are by weight and all temperatures are in degrees Celsius unless otherwise indicated.

EXAMPLES

Example 1

DTPA-TMDX

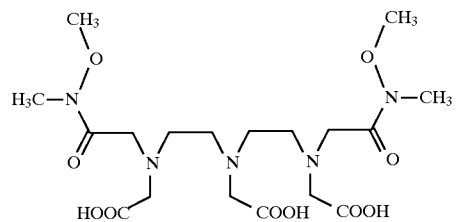

N,O-Dimethylhydroxylamine hydrochloride (16.0 g/164 mmol) was added to dry acetonitrile (60 ml) together with diisopropylethylamine (34.5 ml/198 mmol). The solution was stirred at ambient temperature until the amines were dissolved (10 minutes). DTPA bisanhydride (6.0 g/16.8 mmol) was then added in portions over 2 minutes. 10 minutes after addition ended, all the anhydride had gone into solution. The mixture was stirred overnight, and acetic acid (11.4 ml/198 mmol) was then added. The mixture was evaporated down to an oily residue which was dissolved in water and applied on an AG1-X8 ion exchange column (acetate form) at pH 9.5. The column was washed with water before the product was eluted with 0.5M acetic acid. The chromatographic procedure was repeated twice to give the title compound. Yield 3.5 g, (43% of theory). The white solid was recrystalized twice from IPA.

$^1$H NMR ($D_2O$): C$\underline{H}_3$—O 3.48 (s, 6H); C$\underline{H}_3$—N 2.98 (s, 6H); N—C$\underline{H}_2$—CO 4.4 (s, 4H), 3.62 (s, 4H), 3.29 (s, 2H); N—C$\underline{H}_2$—C$\underline{H}_2$—N 2.9 (m, 4H), 3.3 (m, 4H).

Water: 4.0%.

Titration: Purity about 98%.

FAB-MS: MH+: 480 (83%), 422 (17%), 203 (100%).

Example 2

Gd-DTPA-TMDX

DTPA-TMDX (50 mg/0.104 mmol) was dissolved in water (2.0 ml) and $GdCl_3.6H_2O$ (36 mg/0.97 mmol) in water (3 ml) was added. The pH was adjusted to 6.74 with 2N NaOH, and the sample was lyophilized to give the title compound. Relaxivity $R_1$=4.21 mmol$^{-1}$ sec$^{-1}$ and $R_2$=5.14 mmol$^{-1}$ sec$^{-1}$ in water at 10 MHz, 37° C.

Example 3

DTPA-TMHZ

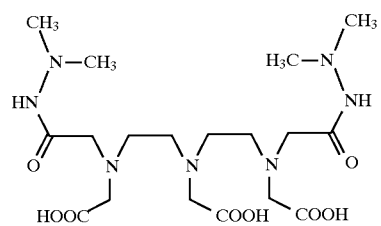

1,1-Dimethylhydrazine (6.1 ml/80.6 mmol) and diisopropylethylamine (17.6 ml/101 mmol) were dissolved in dry acetonitrile (400 ml) at ambient temperature. DTPA bisanhydride (12.0 g/33.6 mmol) was added as a powder in portions over 10 minutes under a $N_2$ atmosphere and with mechanical stirring. The solution was stirred overnight. Diethylether (600 ml) was then added dropwise, and the mixture was stirred for an additional 24 hours before the solvents were decanted off. The remaining precipitate was dissolved in water to a volume of 150 ml. The pH was adjusted to 9 with 2N NaOH, and the solution was applied on an AG1-X8 ion exchange column (acetate form). After washing of the column with water (2900 ml), the product was eluted with 0.5M acetic acid. Collected fractions containing the product were combined and lyophilized to yield 9.2 g (57%) of the title compound. The material was recrystallized twice from water/IPA/acetone.

$^1$H-NMR ($D_2O$,pH6.8): δ 2.29 (s, 12H); 2.82(t,4H); 2.97 (s, 4H); 3.07 (t,4H); 3.13 (s, 4H); 3.55 (s, 2H). FAB-MS: MH+: 478 (100%), 420 (20%) 202 (70%).

Example 4

Gd-DTPA-TMHZ

DTPA-TMHZ (50 mg/0.104 mmol) was dissolved in water (2.0 ml) and $GdCl_3.6H_2O$ (35 mg/0.94 mmol) in water (3 ml) was added. The pH was adjusted to 6.68 with 2N NaOH, and the sample was lyophilized to give the title compound. Relaxivity $R_1$=4.86 mmol$^{-1}$ sec$^{-1}$ and $R_2$=5.40 mmol$^{-1}$ sec$^{-1}$ in water at 10 MHz, 37° C.

Example 5

DTPA(DEHZ)$_2$

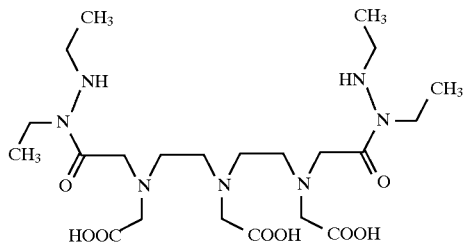

1,2-Diethyl hydrazine dihydrochloride (1.61 g, 10 mmol) and diisopropylethylamine (4.52 g, 35 mmol) are dissolved in dry acetonitrile (50 ml) at ambient temperature. DTPA bisanhydride (2.95 g, 8.25 mmol) is added as a powder in portions over 10 minutes under an $N_2$ atmosphere. The solution is stirred overnight. Diethyl ether (75 ml) is then added dropwise, this mixture is stirred an additional 24 hours and the solvents decanted; the remaining precipitate is dissolved in water (20 ml). The pH adjusted to 9 with 2N NaOH and the solution is applied to AG1-X8 ion exchange column (acetate form). After washing with water the product is eluted with 0.5M acetic acid.

Example 6

O-Bz-DTPA-DX

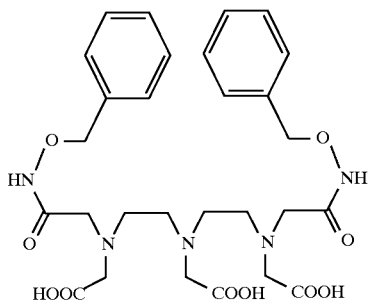

O-Benzylhydroxylamine (4.47 g/28 mmol) was stirred at ambient temperature in dry acetonitrile (150 ml) together with diisopropylethylamine (6.5 ml/37 mmol) until a clear solution was obtained (0.5 hours). DTPA bisanhydride (1.0 g/2.8 mmol) was added as a powder, and the resulting mixture was stirred overnight. Acetic acid (2.2 ml/37 mmol) was added and the solution was evaporated to an oily residue which was dissolved in water. The pH was adjusted to 0.5 with 2N NaOH and the mixture was applied on an AG1-X8 ion exchange column (acetate form). The column was flushed with water (1000 ml) and 0.5N acetic acid (600 ml) before the product was eluted with 2N acetic acid. The fractions containing the product were rechromatographed using 1N acetic acid in methanol:water (1:1 by volume) as eluent to give the title compound (50 mg).

$^1$H-NMR ($D_2O$): Ph—$\underline{H}$7.17 (s); Ar—C$\underline{H}_2$4.65 (s); N—C$\underline{H}_2$—CO 3.4–3.5; N—C$\underline{H}_2$—C$\underline{H}_2$—N 2.6–3.0 (m).

Example 7

Relaxivity of DTPA-DX-(2-isopropyl)$_2$

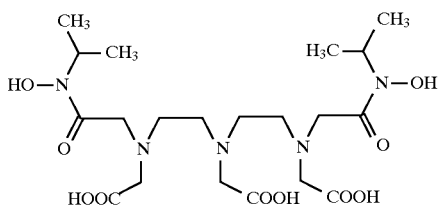

The relaxivity of Gd DTPA-DX-(2-isopropyl)$_2$ (prepared as described for example by Turowski et al. in Inorganic Chemistry 27:474–481(1988)) in water at a concentration range of 16 mM to 0.08 mM was determined to be 6.7 mM$^{-1}$s$^{-1}$. Measurements were performed at 10 MHz and 37° C.

Example 8

O-Bz-EDTA-DX

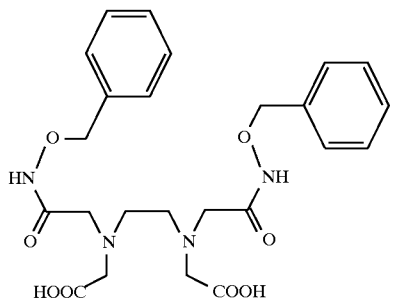

5N NaOH (50 ml) was poured into a 125 ml separating funnel. O-Benzyl-hydroxylamine-HCl (11.2 g/0.07 mol) was added and extracted with $CH_2Cl_2$ (3×35 ml). The extract was washed with water, dried with $Na_2SO_4$ and concentrated to an oil in a rotovap. The oil was diluted with pyridine, EDTA-bisanhydride (7.7 g/0.03 mol) was added and the mixture was stirred using a stir bar under $N_2$. The pyridine was removed using a rotovap (65° C., pump). The glassy residue was dissolved in hot IPA (100 ml). The solvent was removed under vacuum yielding a foamy solid which was dissolved in hot IPA (150 ml). Ethyl acetate (400 ml) was added forming a gummy precipitate. The supernatant was decanted and diethylether was stirred into it and the mixture was chilled. The white precipitate formed (the "second crop") was filtered and dried (6 g). The gummy precipitate was dissolved in methanol (150 ml) and cooled. Ethyl acetate (100 ml) and diethylether (100 ml) were added and the mixture was allowed to stand for 30 minutes. The precipitate formed was filtered and dried (6 g). One gram of the second crop was used for a hydrogenolysis experiment. The remaining dried precipitate (ca. 12 g) was dissolved in hot methanol (ca. 100 ml) and filtered. Ethyl acetate (200 ml) was added and the mixture was stirred for 2 hours. The precipitate was filtered and dried in vacuo. Yield: 10 g. Mpt. 117°–119° C.

Example 9

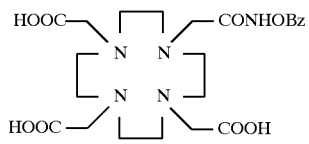

O-Benzylhydroxamic acid DO3A a) Cyclen 1,4,7,10-Tetrazacyclodecane tetrahydrochloride (66.6 g, 209 mmol) was suspended in $CHCl_3$ (2L) and ammonia gas was bubbled through the solution for 1 hour. The solution was allowed to stir overnight. The white solid was filtered off and was washed with four 100 mL portions of $CHCl_3$. The filtrate was combined with the $CHCl_3$ washings and was concentrated by rotary evaporation. The resulting white solid was washed with four 50 mL portions of diethyl ether and was dried under vacuum to give the title compound (31.5 g). A second crop (3.7 g) could be obtained by concentrating the ether washings.

$^1$H-NMR ($CDCl_3$): N—$CH_2$—$CH_2$—N 2.71 (4H, s); N—$H$ 2.35 (1H, s).

b) 1,4,7,10-Tetrazacyclodecane-4,7,10-triacetic acid tri-t-butyl ester monohydrobromide salt Sodium acetate (50.0 g, 609 mmol) was added to a stirred suspension of cyclen (35.0 g, 203 mmol) in N,N-dimethylacetamide (DMA) (600 mL) at ambient temperature. After 0.5 hours, a solution of t-butylbromoacetate (118.9 g, 609 mmol) in DMA (150 mL) was added dropwise under $N_2$. The mixture was stirred at ambient temperature under $N_2$ for 19 days. The white solid was collected by filtration, was washed with ice-cold DMA (75 mL) and ethyl acetate (100 mL), and was dried under vacuum at 50° C. to give 80.2 g of product plus sodium acetate. A second crop of 38.4 g could be collected by concentrating the filtrate to approximately 500 mL and isolating the solid as above. The combined solids were dissolved in $CHCl_3$ (600 mL) and were washed with four 100 mL portions of deionized $H_2O$. The $CHCl_3$ layer was dried over anhydrous $Na_2SO_4$, filtered and concentrated to give the title compound as a white solid (67.4 g).

$^1$H-NMR ($CDCl_3$): NC$H_2$CO$_2$C(CH$_3$)$_3$ 3.22 (4H, s); NC$H_2$CO$_2$C(CH$_3$)$_3$ 3.23 (2H, s); NC$H_2$C$H_2$—N 3.04 (4H, bs); N—CH$_2$CH$_2$—N 2.86 (m); NCH$_2$CO$_2$(C$H_3$)$_3$ 1.40 (27H, s).

c) ClCH$_2$CONHOBz

O-Benzylhydroxylamine hydrochloride (5.0 g) was treated with NaOH (5N, 200 mL) and extracted with ether (200 mL). The ether layer was washed with water, dried over anhydrous magnesium sulphate, filtered and concentrated to yield the free base as a yellow oil (4.06 g).

$^1$H-NMR ($CDCl_3$): 7.35 (s, Ar—H); 5.35 (br, s, NH$_2$); 4.68 (s, OCH$_2$).

O-Benzylhydroxylamine (4.06 g, 33 mmol) and triethylamine (4.7 mL, 33 mmol) were dissolved in chloroform (50 mL) and cooled under nitrogen to −30° C. A solution of chloroacetylchloride (2.63 mL, 33 mmol) in chloroform (15 mL) was added dropwise over a period of 45 minutes. The light green solution was allowed to warm to ambient temperature and stirred for 7 hours. After the addition of water (20 mL), the organic layer was removed and washed with saturated sodium bicarbonate solution (20 mL) and water (20 mL). The organic layer was dried over anhydrous magnesium sulfate, filtered and concentrated to obtain the crude product as a light blue solid (6.02 g). This material was suspended in a mixture of 1:1 ether/chloroform (100 mL) overnight, filtered and washed with ether (30 mL). The solid was dried under vacuum (4.85 g, 74%).

$^1$H-NMR ($CDCl_3$): 8.79 (br, NH); 7.39 (s, Ar—H); 4.93 (s, OCH$_2$); 4.03 (s, COCH$_2$).

d) O-Benzylhydroxamic acid DO3A-tri-t-butyl ester

To a stirred solution of DO3A-tri-t-butyl ester (8.0 g, 13.4 mmol) in acetonitrile (60 mL) was added O-chloro-N-benzylhydroxamic acid (2.7 g, 14.4 mmol). Tetramethylguanidine (3.3 mL, 26.9 mmol) was then added followed by additional acetonitrile (50 mL). The mixture was placed under a stream of $N_2$, heated to 60° C., and stirred for three days. The resulting golden brown solution was concentrated to give a yellow residue which was taken up in chloroform (70 mL) and washed with water (3×40 mL). The organic phase was dried (MgSO$_4$), filtered, and concentrated first on a rotary evaporator and then under vacuum to yield 10.6 g (116%) of a reddish brown oil.

$^1$H-NMR ($CDCl_3$): δ (m, 12H), 2.46 (s, 4H), 1.43 (s, 9H), 1.41 (s, 18H).

e) DO3A-O-benzylhydroxamic acid

To a stirred solution of O-benzylhydroxamic acid DO3A-tri-t-butyl ester (150 mg, 0.220 mmol) in methylene chloride (4 mL) was added a mixture of trifluoroacetic acid (8 mL) and methylene chloride (4 mL). After stirring for three hours at ambient temperature, the solution was concentrated and then redissolved in a mixture of trifluoroacetic acid (8 mL) and methylene chloride (8 mL). The solution was stirred at ambient temperature for seven hours and then concentrated to give a brown oil which was chased with chloroform (4×10 mL) and then water (3×10 mL). The oil was then dissolved in 4M NaOH (10 mL) and washed with chloroform (3×10 mL). Concentration of the aqueous phase gave a thick brown oil which was placed under vacuum to give 130 mg of a biege solid.

$^1$H-NMR (D$_2$O): δ 7.21 (br, 5H), 3.85–2.37 (br, 26H).

Example 10

The gadolinium chelate of O-benzylhydroxamic acid Do3A (Example 9) is prepared analogously to Example 2. Relaxivity $R_1$=4.42 mmol$^{-1}$ sec$^{-1}$ and $R_2$=4.62 mmol$^{-1}$ sec$^{-1}$ in water at 10 MHz, 37° C. (corresponding figures measured in plasma are $R_1$=5.31 and $R_2$=6.77 mmol$^{-1}$ sec$^{-1}$ respectively).

We claim:

1. A macrocyclic compound of formula I

A(X(CR$^1$R$^2$)$_n$)$_m$XA    (I)

or a chelate complex or salt thereof, wherein in formula I, each of the groups R$^1$ and R$^2$ may independently represent a hydrogen atom;

each X independently represents a group NA;

each A independently represents a hydrogen atom or an alkyl group optionally substituted by a group Y, with the proviso that one or more pairs of A groups on different X moieties together form a group (CR$^1$R$^2$)$_n$, thereby forming a macrocyclic compound, each Y represents a hydrogen atom, or a group Z, COZ, SO$_3$R$^6$, CSZ, PO$_2$Z, or B;

each group B represents a group CONR$^7$(NR$^8$$_2$), PO(NR$^7$R$^8$)$_2$, SO$_2$R$^7$, SO$_2$NR$^7$R$^8$, or NO$_2$;

each group Z independently represents a group OR$^6$, SR$^6$, or NR$^6$$_2$;

each of the groups R$^6$ independently represents a hydrogen atom, or an alkyl group optionally substituted by one or more hydroxy or alkoxy or aryl groups;

each of the groups R$^7$ and R$^8$ independently represents a group R$^6$, an aryl group optionally substituted by one or more hydroxy or alkoxy groups, or a lipophilic group;

m is 3;

n is an integer of 2 to 3;

with the provisos that:

(1) at least two non-B ionizable Y groups are present; and (2) at least one Y group represents a non-ionizable group B.

2. A compound of formula I as claimed in claim 1 of formula Ib:

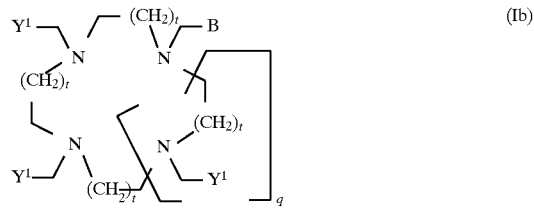

where B is CONR$^7$(NR$^8$$_2$) and q is 1, t is 1, and Y$^1$ is an ion forming group Y.

3. A compound of the formula Ib as claimed in claim 2, wherein Y$^1$ is a carboxyl or carboxylate group.

4. A macrocyclic compound of formula Ic

A(X(CH$_2$)$_2$)$_3$XA    (Ic)

or a chelate complex or salt thereof wherein in formula Ic, each X represents a group NA;

each A independently represents a hydrogen atom or an alkyl group optionally substituted by a group Y, with the proviso that the two terminal A groups together form a group (CH$_2$)$_2$, thereby forming a macrocyclic compound, each Y represents a hydrogen atom, or a group Z, COZ, SO$_3$R$^6$, CSZ, PO$_2$Z, or B;

each group B represents a group CONR$^7$(NR$^8$$_2$), PO(NR$^7$R$^8$)$_2$, SO$_2$R$^7$, SO$_2$NR$^7$R$^8$, or NO$_2$;

each group Z independently represents a group OR$^6$, SR$^6$, or NR$^6$$_2$;

each of the groups R$^6$ independently represents a hydrogen atom, or an alkyl group optionally substituted by one or more hydroxy or alkoxy or aryl groups;

each of the groups R$^7$ and R$^8$ independently represents a group R$^6$, an aryl group optionally substituted by one or more hydroxy or alkoxy groups, or a lipophilic group;

with the provisos that:

(1) at least two non-B ionizable Y groups are present; and (2) at least one Y group represents a non-ionizable group B.

5. A compound as claimed in claim 1, wherein R$^7$ is an optionally substituted alkyl or aryl group, or a lipophilic group and R$^8$ is hydrogen, methyl, benzyl,

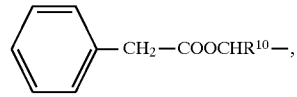

or (CH$_3$)$_3$CCOOCHR$^{10}$—, where R$^{10}$ is hydrogen or an optionally hydroxyl or alkoxy substituted alkyl group, the phenyl moieties of which are optionally substituted by hydroxyl, alkoxy, alkoxyalkyl, hydroxyalkyl, hydroxyalkyl, hydroxyalkoxy, or alkoxyalkoxy groups.

6. A macrocyclic compound as claimed in claim 4

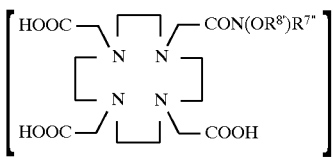 (Ib')

wherein $R^7$ is a lipophilic group and $R^8$ is hydrogen, methyl, benzyl,

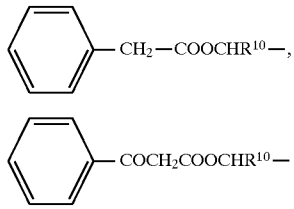

or $(CH_3)_3CCOOCHR^{10}—$, where $R^{10}$ is hydrogen or an optionally hydroxyl or alkoxy substituted alkyl group, the phenyl moieties of which are optionally substituted by hydroxy, alkoxy, alkoxyalkyl, hydroxyalkyl, hydroxyalkoxy, or alkoxyalkoxy groups.

7. A compound of claim 6 wherein $R^7$ is an alkyl, aryl, aralkyl, or alkaryl group and $R^8$ is hydrogen.

8. A process for the preparation of a macrocyclic compound of formula I as defined in claim 1, said process comprising one or more of the following steps
(i) reacting a compound of formula II $$A''(X''(CR^{1''}R^{2''})_n X'')_m A'' \tag{II}$$

where X" is a group X, a protected group X, or a group NA'''; A" is a group A, a protected group A, or a group A'''; A''' is an alkyl group attached to an activated carboxyl or phosphono group;
$R^{1''}$ and $R^{2''}$ are each groups $R^1$ or $R^2$ or protected groups $R^1$ and $R^2$ respectively; with the proviso that at least one group A''' is present,
with an amine derivative of formula III $$B''H \tag{III}$$

where B" is a group, $NR^7NR^8_2$, or $NR^7R^8$ or a protected such group,
followed, if required, by the removal of any protecting groups;
(ii) reacting a compound of formula IV $$A*(X*(CR^{1''}R^{2''})_n X*)_m A* \tag{IV}$$

where A* is a group A, a protected group A or a hydrogen atom; X* is a group X, a protected group X, or a group NA*, and $R^{1''}$, $R^{2''}$, n and m are as hereinbefore defined, with the proviso that at least one A* is hydrogen
with a compound of formula V $$Lv—A** \tag{V}$$

where Lv is a leaving group and A** is a Y-containing A or protected A group,
followed, if required, by the removal of any protecting groups;
(iii) converting a compound of formula I into a salt thereof or a salt of a compound of formula I into the free acid or base; and (iv) converting a compound of formula I or salt thereof into a chelate complex thereof.

9. A macromolecular derivative of a compound of formula I or a metal chelate or salt thereof as defined in claim 1 in which said compound is linked to a macromolecule or polymer.

10. A diagnostic agent comprising a macrocyclic compound of formula I $$A(X(CR^1R^2)_n)_m XA \tag{I}$$

or a metal chelate of salt thereof, formulated together with or adapted for formulation with at least one pharmaceutical or veterinary carrier or excipient
wherein in formula I
each of the groups $R^1$ and $R^2$ may independently represent a hydrogen atom, or an alkyl or alkoxy group optionally carrying one or more substituents selected from hydroxy, alkoxy and aryl groups;
each X independently represents an oxygen or sulphur atom, or a group NA;
each A independently represents a hydrogen atom or an alkyl group optionally substituted by a group Y, with the proviso that one or more pairs of A groups on different X moieties may together form a group $(CR^1R^2)_n$, thereby forming a macrocyclic ring,
each Y represents a hydrogen atom, or a group Z, COZ, $SO_3R_6$, CSZ, $PO_2Z$, or B;
each group B represents a group $CONR^7(NR^8_2)$, $PO(NR^7R^8)_2$, $SO_2R^7$, $SO_2NR^7R^8$, or $NO_2$;
each group Z independently represents a group $OR^6$, $SR^6$, or $NR^6_2$;
each of the groups $R^6$ independently represents a hydrogen atom, or a alkyl group optionally substituted by one or more hydroxy or alkoxy groups;
each of the groups $R^7$ and $R^8$ independently represents a group $R^6$, an aryl group optionally substituted by one or more hydroxy or alkoxy groups, or a lipophilic group;
m is 3;
n is an integer of 2 to 3;
with the provisos that:
(1) at least two non-B ionizable Y groups are present; and
(2) at least one Y group represents a non-ionizable group B.

11. A diagnostic agent as claimed in claim 10 of formula Ib or a metal chelate or salt thereof

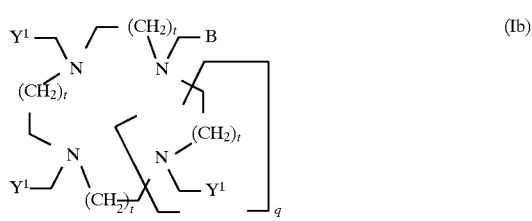 (Ib)

where B is $CONR^7(NR^8_2)$ and q is 1, t is 1, and $Y^1$ is an ion forming group Y.

12. A diagnostic agent as claimed in claim 10 or a metal chelate or salt thereof

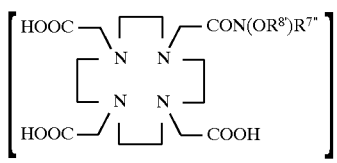

where $R^7$ is a lipophilic group and $R^8$ is hydrogen, methyl, benzyl,

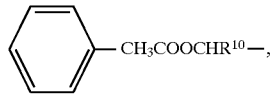

or $(CH_3)_3CCOOCHR^{10}-$, where $R^{10}$ is hydrogen or an optionally hydroxyl or alkoxy substituted alkyl group, the phenyl moieties of which are optionally substituted by hydroxy, alkoxy, alkoxyalkyl, hydroxyalkyl, hydroxyalkoxy, or alkoxyalkoxy groups.

13. A diagnostic agent as claimed in claim 10 of formula Ic $$A(X(CH_2)_2)_3XA \qquad (Ic)$$

or a chelate complex or salt thereof
  wherein in formula Ic,
  each X represents a group NA;
  each A independently represents a hydrogen atom or an alkyl group optionally substituted by a group Y, with the proviso that the two terminal A groups together form a group $(CH_2)_2$, thereby forming a macrocyclic compound,
  each Y represents a hydrogen atom, or a group Z, COZ, $SO_3R^6$, CSZ, $PO_2Z$, or B;
  each group B represents a group $CONR^7(NR^8{}_2)$, $PO(NR^7R^8)_2$, $SO_2R^7$, $SO_2NR^7R^8$, or $NO_2$;
  each group Z independently represents a group $OR^6$, $SR^6$, or $NR^6{}_2$; each of the groups $R^6$ independently represents a hydrogen atom, or an alkyl group optionally substituted by one or more hydroxy or alkoxy or aryl groups;
  each of the groups $R^7$ and $R^8$ independently represents a group $R^6$, an aryl group optionally substituted by one or more hydroxy or alkoxy groups, or a lipophilic group;
  with the provisos that:
    (1) at least two non-B ionizable Y groups are present; and
    (2) at least one Y group represents a non-ionizable group B.

14. A method of generating enhanced images of the human or non-human animal body, which method comprises administering to said body a diagnostic agent comprising a metal chelate or a salt thereof of a compound of claim 10.

15. A process for the preparation of a metal chelate of a compound of formula I as defined in claim 1, which comprises admixing in a solvent said compound, or a salt or chelate thereof, together with an at least sparingly soluble compound of said metal.

16. A process for the preparation of a diagnostic agent which comprises admixing a metal chelate of a compound of claim 10, or a physiologically acceptable salt thereof, together with at least one pharmaceutical or veterinary carrier or excipient.

* * * * *